(12) United States Patent
Adlaf et al.

(10) Patent No.: US 9,533,930 B2
(45) Date of Patent: *Jan. 3, 2017

(54) METHODS FOR PRODUCING BIODERIVED PROPYLENE GLYCOL

(71) Applicant: ARCHER DANIELS MIDLAND COMPANY, Decatur, IL (US)

(72) Inventors: Kevin J. Adlaf, Forsyth, IL (US); Paul D. Bloom, Forsyth, IL (US); William Chris Hoffman, Decatur, IL (US); Chicheng Ma, Forsyth, IL (US); John G. Soper, Mt.Zion, IL (US); Brad Zenthoefer, Decatur, IL (US)

(73) Assignee: Archer-Daniels-Midland-Company

( * ) Notice: Subject to any disclaimer, the term of this patent is extended or adjusted under 35 U.S.C. 154(b) by 0 days.

This patent is subject to a terminal disclaimer.

(21) Appl. No.: 14/613,877

(22) Filed: Feb. 4, 2015

(65) Prior Publication Data
US 2015/0152031 A1    Jun. 4, 2015

Related U.S. Application Data

(63) Continuation of application No. 14/279,395, filed on May 16, 2014, now abandoned, which is a continuation of application No. 14/002,160, filed on Oct. 10, 2013, now abandoned.

(51) Int. Cl.
| | | |
|---|---|---|
| *C07C 29/80* | (2006.01) | |
| *C07B 63/00* | (2006.01) | |
| *C07C 29/88* | (2006.01) | |
| *C07C 31/20* | (2006.01) | |
| *B01D 3/14* | (2006.01) | |
| *C07C 29/76* | (2006.01) | |
| *B01D 3/34* | (2006.01) | |
| *B01D 15/36* | (2006.01) | |
| *C07C 29/60* | (2006.01) | |

(52) U.S. Cl.
CPC ............... *C07C 29/80* (2013.01); *B01D 3/143* (2013.01); *B01D 3/34* (2013.01); *B01D 15/362* (2013.01); *C07B 63/00* (2013.01); *C07C 29/60* (2013.01); *C07C 29/76* (2013.01); *C07C 29/88* (2013.01); *C07C 31/20* (2013.01); *C07C 31/202* (2013.01); *C07C 31/205* (2013.01)

(58) Field of Classification Search
None
See application file for complete search history.

(56) References Cited

U.S. PATENT DOCUMENTS

2011/0112335 A1*    5/2011    Godavarthy et al. ......... 568/861

FOREIGN PATENT DOCUMENTS

WO    2010102361    *    9/2010

* cited by examiner

*Primary Examiner* — Karl J Puttlitz
(74) *Attorney, Agent, or Firm* — William B Miller

(57) ABSTRACT

In the process of distilling a polyol product mixture including one or both of a biobased propylene glycol and a biobased ethylene glycol from the reaction of hydrogen with a biobased feed, it has been discovered that undesirable epoxides can form, and the present invention provides means for guarding against their formation, for removing epoxides which do form by particular methods of distilling, and for removing the epoxides from a finished, otherwise commercially acceptable biobased glycol product.

2 Claims, 3 Drawing Sheets

METHODS FOR PRODUCING BIODERIVED PROPYLENE GLYCOL

CROSS REFERENCE TO RELATED APPLICATIONS

This application is a continuation of U.S. patent application Ser. No. 14/279,395, filed May 16, 2014, which is a continuation of U.S. patent application Ser. No. 14/002,160, filed Oct. 10, 2013.

TECHNICAL FIELD

This invention relates generally to processes for making a bioderived propylene glycol. More particularly, the present invention relates to methods for making a bioderived propylene glycol through the reaction of a biobased feedstock—conventionally, glycerol or five and six carbon sugars and/or sugar alcohols—with hydrogen to provide a polyol product mixture including propylene glycol, wherein the polyol product mixture is further processed to yield a commercially acceptable biobased equivalent to the petroleum-based or -derived commodity propylene glycol product used today in so many different applications.

BACKGROUND

The present invention is concerned with the development of renewably sourced products which are able to serve as commercially acceptable, drop in replacements for materials, and especially commodities such as propylene glycol and ethylene glycol, which are presently made downstream of conventional fossil fuel operations. Such biobased, renewably sourced materials can be differentiated from their petroleum-derived counterparts, for example, by their carbon isotope ratios using ASTM International Radioisotope Standard Method D 6866, the disclosure of which is incorporated by reference in its entirety. Method D 6866 is based upon the fact that isotopic ratios of the isotopes of carbon within any given material, such as the 13C/12C carbon isotopic ratio or the 14C/12C carbon isotopic ratio, can be determined using certain established analytical methods, such as isotope ratio mass spectrometry, with a high degree of precision.

ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D 6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products. As used herein, "biologically derived", "bioderived", and "biobased" may be used interchangeably to refer to materials whose carbon content is shown by ASTM D 6866, in whole or in significant part (for example, at least about 20 percent or more), to be derived from or based upon biological products or renewable agricultural materials (including but not limited to plant, animal and marine materials) or forestry materials.

Propylene glycol and ethylene glycol have conventionally been produced from petrochemical sources. Commercial production of petroleum-based or -derived propylene glycol involves the hydration of propylene oxide, made predominantly by the oxidation of propylene. The commercial production of ethylene glycol similarly involves the hydration of ethylene oxide, made by the oxidation of ethylene. Propylene and ethylene in turn are industrial by-products of gasoline manufacture, for example, as by-products of fluid cracking of gas oils or steam cracking of hydrocarbons.

The world's supply of petroleum is, however, being depleted at an increasing rate. As the available supply of petroleum decreases or as the costs of acquiring and processing the petroleum increase, the manufacture of various chemical products derived therefrom (such as propylene glycol and ethylene glycol) will be made more difficult. Accordingly, in recent years much research has taken place to develop suitable biobased propylene glycol and ethylene glycol products, which can be interchangeable with propylene glycol and ethylene glycol products deriving from petroleum refining and processing methods but which are made from renewable versus nonrenewable materials.

As a result of these efforts, processes have been developed by several parties involving the hydrogenolysis of especially five and six carbon sugars and/or sugar alcohols, whereby the higher carbohydrates are broken into fragments of lower molecular weight to form compounds which belong to the glycol or polyol family. Sugars containing five carbon chains, such as ribose, arabinose, xylose and lyxose, and corresponding five carbon chain sugar alcohols such as xylitol and arabinitol, are among the materials contemplated in U.S. Pat. No. 7,038,094 to Werpy et al., for example, as are six carbon sugars such as glucose, galactose, maltose, lactose, sucrose, allose, altrose, mannose, gulose, idose and talose and six carbon chain sugar alcohols such as sorbitol. Some of these carbohydrate-based feedstocks are commercially available as pure or purified materials. These materials may also be obtained as side-products or even waste products from other processes, such as corn processing. The sugar alcohols may also be intermediate products produced in the initial stage of hydrogenating a sugar.

For other known examples of such processes, U.S. Pat. No. 5,206,927 describes a homogeneous process for hydrocracking carbohydrates in the presence of a soluble transition metal catalyst to produce lower polyhydric alcohols. A carbohydrate is contacted with hydrogen in the presence of a soluble transition metal catalyst and a strong base at a temperature of from about 25° C. to about 200° C. and a pressure of from about 15 to about 3000 psi. However, as is evident from Tables II and III in the disclosure of U.S. Pat. No. 5,206,927, about 2-7% of other polyol compounds are produced in the hydrocracking process. U.S. Pat. No. 4,476, 331 describes a two stage method of hydrocracking carbohydrates using a modified ruthenium catalyst. European Patent Applications EP-A-0523 014 and EP-A-0 415 202 describe a process for preparing lower polyhydric alcohols by catalytic hydrocracking of aqueous sucrose solutions at elevated temperature and pressure using a catalyst whose active material comprises the metals cobalt, copper and manganese. Still other examples of such carbohydrate-based processes may be found without difficulty by those skilled in the art.

Other efforts have been based on the use of another readily accessible biobased feedstock, namely, glycerol. Glycerol is currently produced as a byproduct in making biodiesel from vegetable and plant oils, through the trans-esterification reaction of lower alkanols with higher fatty acid triglycerides to yield lower alkyl esters of higher fatty acids and a substantial glycerol byproduct. Glycerol is also available as a by-product of the hydrolysis reaction of water with higher fatty acid triglycerides to yield soap and glycerol. The higher fatty acid triglycerides may derive from animal or vegetable (plant) sources, or from a combination of animal and vegetable sources as well known, and a variety of processes have been described or are known.

In the context of vegetable oil-based biodiesel production and soap making, all sorts of vegetable oils have been combined with the lower aliphatic alcohols or water. Preferred vegetable oils include, but are not limited to, soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives, conjugated derivatives, genetically-modified derivatives and mixtures thereof. As used herein, a reference to a vegetable oil includes all its derivatives as outlined above. For instance, the use of the term "linseed oil" includes all derivatives including conjugated linseed oil.

A biobased glycerol is also available as a product of the hydrogenolysis of sorbitol, as described in an exemplary process in U.S. Pat. No. 4,366,332, issued Dec. 28, 1982.

U.S. Pat. Nos. 5,276,181 and 5,214,219 thus describe a process of hydrogenolysis of glycerol using copper and zinc catalyst in addition to sulfided ruthenium catalyst at a pressure over 2100 psi and temperature between 240-270° C. U.S. Pat. No. 5,616,817 describes a process of preparing 1,2-propanediol (more commonly, propylene glycol) by catalytic hydrogenolysis of glycerol at elevated temperature and pressure using a catalyst comprising the metals cobalt, copper, manganese and molybdenum. German Patent DE 541362 describes the hydrogenolysis of glycerol with a nickel catalyst. Persoa & Tundo (Ind. Eng. Chem. Res. 2005, 8535-8537) describe a process for converting glycerol to 1,2-propanediol by heating under low hydrogen pressure in presence of Raney nickel and a liquid phosphonium salt. Selectivities toward 1,2-propanediol as high as 93% were reported, but required using a pure glycerol and long reaction times (20 hrs). Crabtree et al. (Hydrocarbon processing February 2006 pp 87-92) describe a phosphine/precious metal salt catalyst that permit a homogenous catalyst system for converting glycerol into 1,2-propanediol. However, low selectivity (20-30%) was reported. Other reports indicate use of Raney copper (Montassier et al. Bull. Soc. Chim. Fr. 2 1989 148; Stud. Surf. Sci. Catal. 41 1988 165), copper on carbon (Montassier et al. J. Appl. Catal. A 121 1995 231)), copper-platinum and copper ruthenium (Montassier et al. J. Mol. Catal. 70 1991 65). Still other homogenous catalyst systems such as tungsten and Group VIII metal-containing catalyst compositions have been also tried (U.S. Pat. No. 4,642,394). Miyazawa et al. (J. Catal. 240 2006 213-221) &

Kusunoki et al (Catal. Comm. 6 2005 645-649) describe a Ru/C and ion exchange resin for conversion of glycerol in aqueous solution. Again their process however, results in low conversions of glycerol (0.9-12.9%). Again, still other examples of like processes may be found without difficulty by those skilled in the art.

One of the recognized problems in producing a biobased propylene glycol or ethylene glycol by such methods, is that other diol compounds are formed which reduce the purity of the desired component. The boiling points of many of these components as shown in Table A are very close to one another, however, so that the separation of substantially pure propylene glycol from these other polyhydric alcohols is difficult.

TABLE A

Polyols produced by Hydrocracking of Sorbitol

| Polyol | Weight Percent | Boiling Point, ° C. |
|---|---|---|
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerin | 38.8 | 290 |
| 1,2,4-Butanetriol | 4.8 | 190/18 mm |

Several reports in the literature describe efforts for azeotropically separating the other polyhydric alcohols from propylene glycol. For instance, U.S. Pat. No. 4,935,102 describes a method for using an azeotrope forming agent such as propylene glycol isobutyl ether, tetrahydrofurfuryl alcohol, N,N-dimethylacetamide, ethylene glycol diethyl ether, diethylene glycol diethyl ether, 2-methoxyethyl ether, ethylene glycol n-butyl ether, diacetone alcohol and ethyl n-butyl ketone. In U.S. Pat. No. 5,423,955, the azeotrope forming agent consists of a material selected from the group consisting of toluene, ethyl benzene, o-xylene, p-xylene, cumene, m-diisopropyl benzene, m-diethyl benzene, mesitylene, p-cymene, hexane, cyclohexane, methyl cyclohexane, heptane, 3-methyl pentane, octane, decane, 2,3,4-trimethyl pentane, dipentene, decalin, dicyclopentadiene, alpha-phellandrene, limonene, hemimellitene, myrcene, terpinolene, p-mentha-1,5-diene, beta-pinene, 3-carene, 1-heptene, cyclopentane, pentane, o-diethyl benzene, 2,2-dimethyl butane and 2-methyl butane. The azeotrope forming agents described in these two references may be characterized by their Hansen solubility parameters (Tables B and C), as these can be determined using the program "Molecular Modeling Pro Plus (version 6.0.6, Norgwyn Montgomery Software Inc, available from ChemSW, Inc) based on values published in the "Handbook of Solubility Parameters and Other Parameters" by Allen F. M. Barton (CRC Press, 1983) for solvents obtained experimentally by Hansen. The Hansen "h" (hydrogen bonding) values at 25° C. and Hansen "p" (polarity) values ° C. listed below were calculated in this manner.

TABLE B

Azeotropic agents used for separation of 2,3-Butanediol
from propylene glycol (U.S. Pat. No. 4,935,102).

| Azeotropic agent | Hansen p | Hansen h |
| --- | --- | --- |
| Propylene glycol isobutyl ether | 5.42 | 12.52 |
| Tetrahydrofurfuryl alcohol | 10.46 | 10.96 |
| N,N-dimethylacetamide | 11.47 | 10.23 |
| Toluene | 0.75 | 1.98 |
| Ethyl benzene | 0.65 | 1.85 |
| p-Xylene | 0.91 | 1.84 |
| m-Xylene | 0.91 | 1.84 |
| o-Xylene | 0.91 | 1.84 |
| Cumene | 0.58 | 1.74 |
| Mesitylene | 0.98 | 1.7 |
| Ethylene glycol diethyl ether | 9.19 | 14.3 |
| Diethylene glycol diethyl ether | 9.22 | 12.33 |
| 2-Methoxyethyl ether | 1.81 | 7.41 |
| Ethylene glycol-n-butyl ether | 5.13 | 12.27 |
| Diacetone alcohol | 8.17 | 10.76 |
| 3-heptanone | 5.28 | 3.93 |

TABLE C

Azeotropic agents used for separation of 1,2-Butanediol
from ethylene glycol (U.S. Pat. No. 5,423,955).

| Azeotropic agent | Hansen p | Hansen h |
| --- | --- | --- |
| 3-Heptanone | 5.28 | 3.93 |
| Cyclohexanone | 3.13 | 5.08 |
| Diisobutyl ketone | 4.9 | 3.79 |
| Methyl isoamyl ketone | 6.03 | 4.2 |
| Isobutyl heptyl ketone | 3.76 | 3.31 |
| 2-Methoxyethyl ether | 1.81 | 7.41 |
| 2,6-Dimethyl-4-heptanone | 4.90 | 3.79 |
| p-Xylene | 0.91 | 1.84 |
| m-Xylene | 0.91 | 1.84 |
| o-Xylene | 0.91 | 1.84 |
| Ethyl benzene | 0.65 | 1.85 |
| Cumene | 0.58 | 1.74 |
| Mesitylene | 0.98 | 1.7 |

Alternative approaches to purifying the product mixture have been proposed in commonly-assigned United States Patent Application Publication US 2008/0275277A1 to Kalagias, published Nov. 6, 2008, wherein the addition of a polar solvent and extractive distillation are presented as an alternative to the use of an azeotropic agent, and in commonly-assigned United States Patent Application Publication US2009/0120878A1 to Hilaly et al., published May 14, 2009, wherein simulated moving bed chromatography is offered as a means to achieve a purified, commercial grade biobased propylene glycol.

A difficulty that has not been appreciated before, though, is that in distilling out these other, undesired polyhydric alcohols, conditions can be such that epoxides such as propylene oxide and glycidol can be formed. These two epoxides in particular are of concern for certain established uses and commercially important applications of propylene glycol, at least for the reason that these substances are listed under the State of California's "The Safe Drinking Water and Toxic Enforcement Act of 1986"—more commonly known as Proposition 65—as being known to California to cause cancer. Consequently, having a biobased, drop-in replacement propylene glycol for a petroleum-based or -derived propylene glycol will depend, for certain markets and end uses at least, on developing a solution or solutions to this heretofore unrecognized problem.

SUMMARY OF THE INVENTION

The present invention addresses this difficulty by providing, according to a first aspect, a process for distilling a product mixture comprised of biobased propylene glycol, biobased ethylene glycol or a combination thereof and which further includes one or both of propylene oxide and glycidol, so that a distilled biobased glycol product stream is produced which is substantially free of both propylene oxide and glycidol. Epoxide removal is thus integrated into the refining process for a crude reaction product, to produce the desired biobased, commercially acceptable glycol product.

In other aspects, the present invention concerns other solutions that can be implemented independently of one another or especially given a preexistent refining process (that may or may not be feasibly adapted or modified to carry out a distillation process according to the first aspect), for example, a process for removing substantially all of the propylene oxide and glycidol present in an otherwise finished, biobased glycol product, as well as a process for guarding against and preferably substantially preventing the formation of propylene oxide and glycidol in a biobased glycol product from the distillation of the aforementioned product mixture. The present invention in this regard also contemplates measures for both guarding against the formation of propylene oxide and glycidol in the biobased glycol product, as well as for treating the biobased glycol product to ensure a biobased glycol product that is substantially free of propylene oxide and glycidol.

DETAILED DESCRIPTION

In its various embodiments, the present invention addresses the need for a biobased glycol product that is compliant with the requirements of Proposition 65 and preferably substantially free of propylene oxide and glycidol.

In one approach, the present invention addresses this difficulty by providing, according to a first aspect, a process for distilling a mixture containing propylene glycol, ethylene glycol, propylene oxide, glycidol and other monools and diols, such as a mixture obtained from the reaction of hydrogen with a sugar or sugar alcohol or with glycerol according to a method of the type described above.

Figure 1:
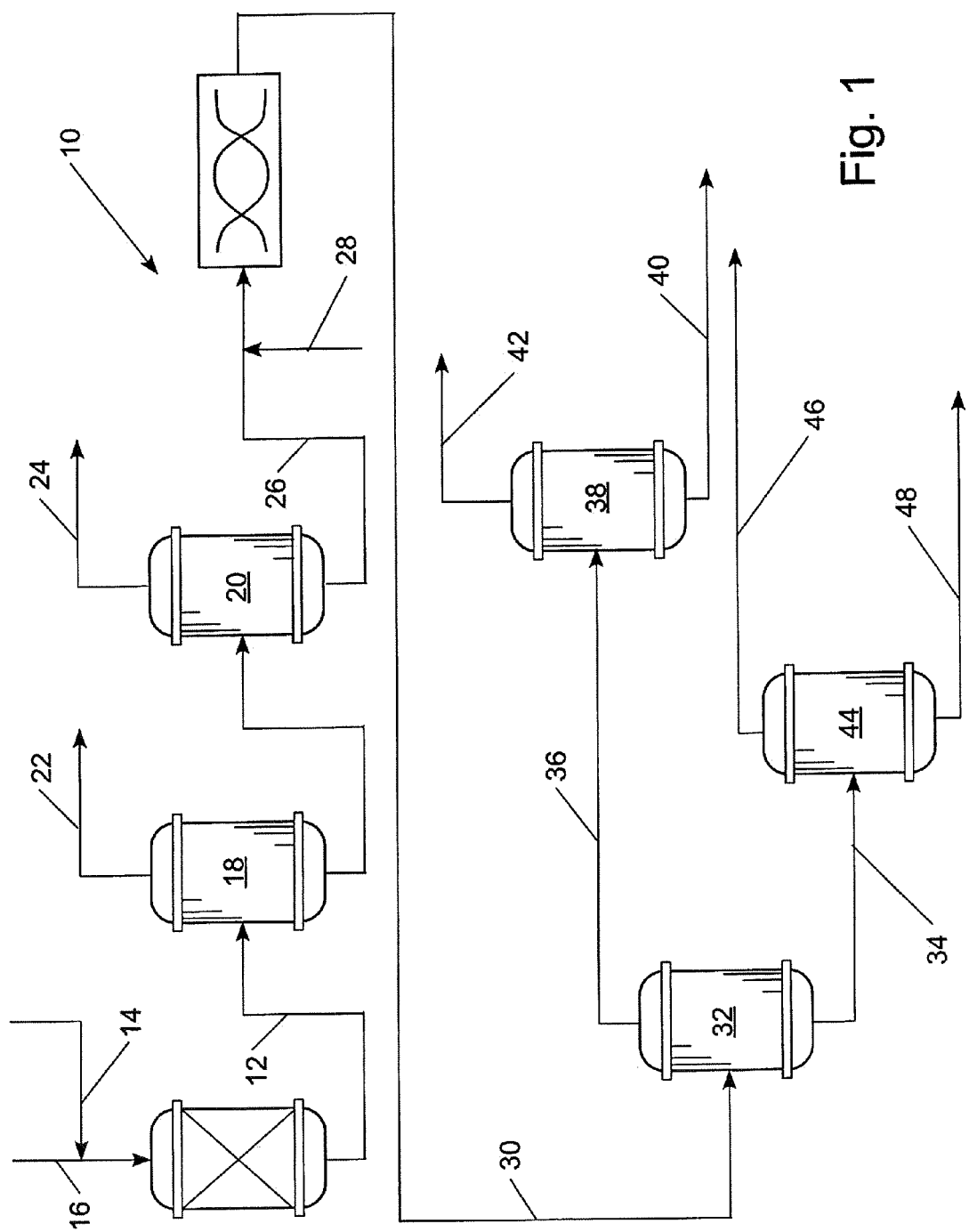
FIG. 1 depicts one embodiment of a distillation process that might be used according to the present invention.

In one embodiment 10 which is schematically depicted in FIG. 1, an aqueous reaction product 12 from the reaction of hydrogen 14 with an aqueous solution of biobased glycerol 16 according to a process of the type described in United States Patent Application Publication US2008/0274019A1 to Beggin et al., published Nov. 6, 2008 and now incorporated herein by reference—and of the same general character as processed in the commonly-assigned Kalagias and Hilaly et al. applications—is first distilled in columns 18 and 20 to remove low molecular weight alcohols (methanol, ethanol, propanols for example) and water overhead in streams 22 and 24, respectively. The remainder 26 is pH modified with an acid 28 as described in the Beggin et al. reference, and then supplied as stream 30 to column 32, wherein components with boiling points higher than that of propylene glycol (unconverted glycerol, mixed diols inclusive of the ethylene glycol formed in the process) are removed in stream 34. The distillate 36 is refined by distillation in column 38 to produce a high purity propylene glycol as a substantially water-free, bottoms product 40, with the glycidol and propylene oxide being removed overhead in stream 42 with any residual water and mixed diols. Stream 34 is preferably further processed by distillation in column 44 to enable recovery of an ethylene glycol-rich diols mix overhead in stream 46 and unreacted glycerol for recycle as desired in stream 48.

Figure 2:
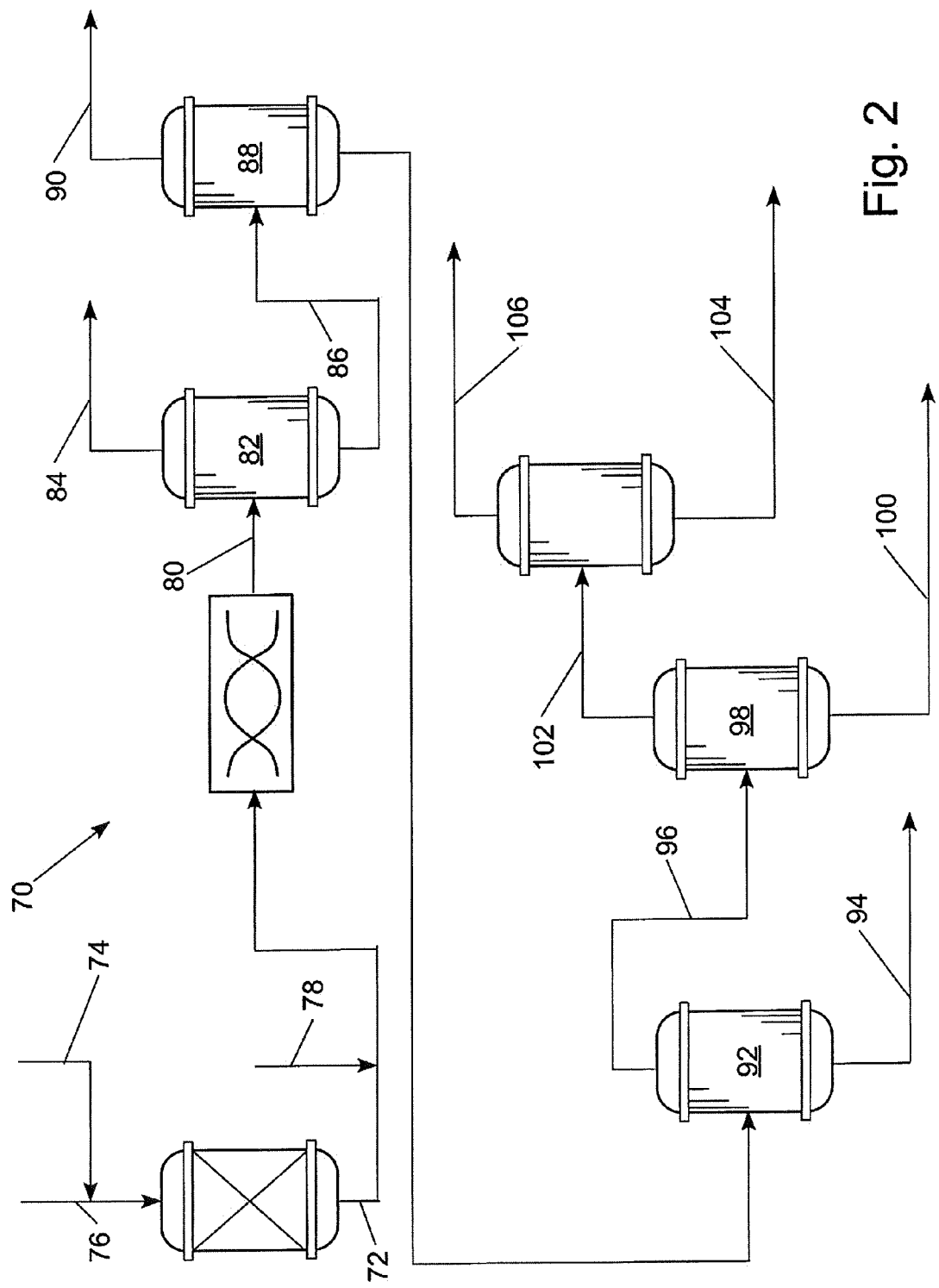
FIG. 2 depicts an alternate embodiment of a distillation process according to the present invention.

In another embodiment 70 of a distillation process, shown schematically in FIG. 2, an aqueous reaction product 72 from the reaction of hydrogen 74 with an aqueous solution of biobased glycerol 76 is first pH modified by the addition at 78 of acid, preferably sulfuric acid, before being supplied as stream 80 to a first column 82. Lower molecular weight alcohols are distilled off in stream 84, then the remainder 86 proceeds to a second column 88 which operates to remove all but a small amount of water as stream 90. Column 92 separates out unreacted glycerol in a bottoms stream 94, and the distillate 96 containing ethylene glycol, propylene glycol, higher diols (e.g., butanediols, pentanediols), propylene oxide, glycidol and less than one percent of water is further refined by distillation in column 98, where ethylene glycol is first separated as a bottoms product 100. From the distillate 102, high purity propylene glycol is separated out as a substantially propylene oxide- and glycidol-free, substantially water-free bottoms product 104, with the propylene oxide, glycidol, 2,3-butanediol and any residual water being removed overhead in stream 106.

Figure 3:
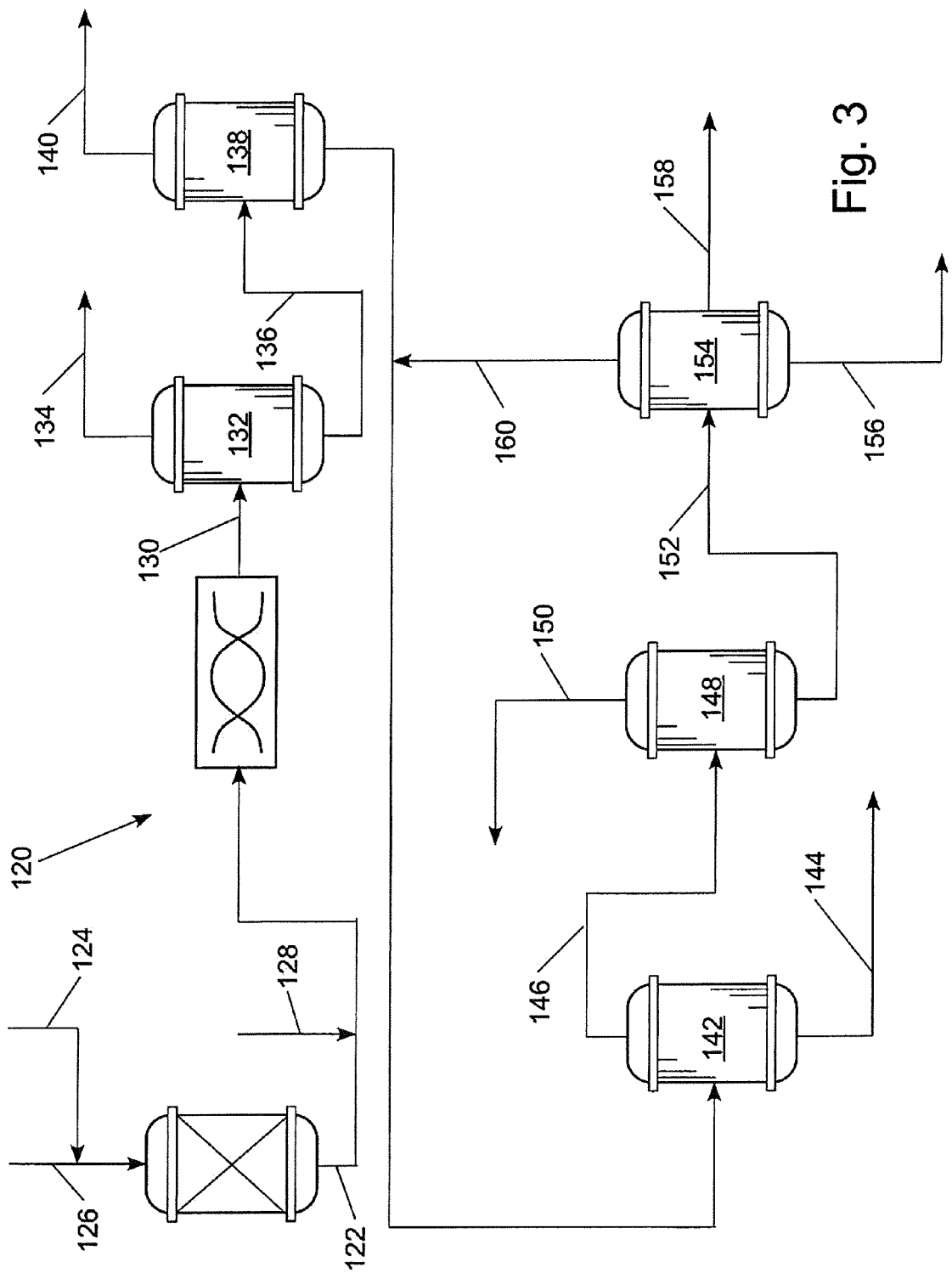
FIG. 3 depicts a second alternate embodiment of a distillation process according to the present invention.

Referring now to FIG. 3, in yet another embodiment 120 of a distillation process of the present invention according to a first aspect, an aqueous reaction product 122 from the reaction of hydrogen 124 with an aqueous solution of biobased glycerol 126 is first pH modified by the addition at 128 of acid, preferably sulfuric acid, before being supplied as stream 130 to a first column 132. Lower molecular weight alcohols are distilled off in stream 134, then the remainder 136 proceeds to a second column 138 which operates to remove all but a small amount of water as stream 140. Column 142 separates out unreacted glycerol in a bottoms stream 144, and the distillate 146 containing ethylene glycol, propylene glycol, higher diols (e.g., butanediols, pentanediols), propylene oxide, glycidol and less than one percent of water is further refined by distillation in column 148. Propylene oxide, glycidol, 2,3-butanediol and any residual water are distilled overhead from the column 148 in stream 150, and the bottoms stream 152 containing ethylene and propylene glycols is further distilled in column 154. A predominantly ethylene glycol bottoms product 156 (with some residual propylene glycol) is recovered from the column 154, while a high purity propylene glycol product 158 is recovered as a substantially glycidol- and propylene oxide-free sidestream from the distillation. Some propylene glycol and residual propylene oxide are carried overhead in 160 for being recycled back to column 142.

In each of these distillation embodiments, propylene oxide and glycidol are thus easily removed from the product mix resulting from the hydrogenolysis of a carbohydrate or polyol, according to any of the various references summarized above. In these distillations, the propylene oxide and glycidol are removed in the distillates. Most of the propylene oxide is removed with the lower molecular weight alcohols, whereas most of the glycidol is removed with the butanediols.

The present invention also provides a solution for removing substantially all of the propylene oxide and glycidol otherwise present in a biobased glycol product, for example, after water, lower molecular weight alcohols, higher diols and unconverted glycerol have all been removed from an otherwise finished, purified and commercially suitable propylene glycol product, by treating the otherwise finished biobased glycol product with strong acid ion exchange resins. Resins suitable for this application include any gel or macroporous (macroreticular) polymer such as polystyrene or polystyrene/divinylbenzene that has been functionalized with sulfonic acid. Examples of suitable commercially available resins presently meeting this description are AMBERLYST 15, AMBERLYST 35, AMBERLITE 200 H, DIAION UBK555 (H+ form), DOWEX 50W, DOWEX 88(H+ form), and PUROLITE PD206. Typical conditions for the treatment of epoxide-containing glycol product streams are flow rates of 1-5 bed volumes/hr and temperatures of 50-120° C., preferably 60-100° C., and most preferably 60-80° C.

A process for guarding against and preferably substantially preventing the formation of propylene oxide and glycidol in a biobased glycol product from the distillation of the aforementioned product mixture, involves simply removing organic acid salts contained in the aqueous reaction product from the hydrogenolysis of a carbohydrate or of a polyol such as glycerol. Preferably all or substantially all of the salts are so removed, for example, at least about 85 percent, more preferably at least about 90 percent and most preferably more than about 96 percent of the salts being removed. Surprisingly, these salts have been found to contribute to the production of epoxides such as propylene oxide and glycidol in the distillation and refining of the aqueous reaction product. Separation and removal of these organic acid salts may be accomplished by ion exclusion chromatography, using resins known to those skilled in the art as suited for this purpose, for example, any of the various sodium or calcium form, strong cation exchange styrene/polystyrene-divinylbenzene copolymer resins such as those available from The Dow Chemical Company under the trade designations DOWEX 99/320, DOWEX 99/290, DOWEX N406, N306 AND N606, AMBERLITE CR1310, CR1320, C20N and IR 120, and AMBERJET 1000Na, 1300Na and 1500 Na, from Mitsubishi Chemical Company under the trade designations UBK550, UBK510L and UBK530, from The Purolite Company under the trade designations C100, PCR145, PCR450, PCR642, PCR732 and PCR833 or from a number of other manufacturers. Simulated moving bed chromatography methods have been found useful for essentially continuously removing the salts, as exemplified below.

The bio-based propylene glycol, the bio-based ethylene glycol or the combination thereof obtained by the processes of the present invention may be subjected to further purification or isolation techniques in order to get a purity of at least 95%. In a further embodiment, the purity may be obtained to at least 99.5% or even 99.7% depending on the desired use of the bio-based propylene glycol, the bio-based ethylene glycol or the combination thereof.

Further, those skilled in the art will appreciate that combinations of the measures offered above may be contemplated, for example, ion exclusion chromatography may be employed to remove organic acid salts from the aqueous reaction product while one of the distillation solutions or treatment with strong acid ion exchange resins may be additionally undertaken to ensure a biobased glycol product that is substantially free of the epoxides that would be present were such measures not taken.

Still other refinements and modifications will be apparent to those skilled in the art given the embodiments that have been described above and in view of the examples that follow, and it is consequently understood that the present invention should not be taken as limited to the particular embodiments or features of embodiments, or to any particular combination of features or details, except as expressly required by the claims which follow.

With this caveat, the present invention is more particularly illustrated and understood by reference to the following examples:

EXAMPLE 1

In this example, the removal of propylene oxide and glycidol are demonstrated from two distillate streams containing propylene glycol (one actually obtained, and one synthesized/simulated to approximate a distillate stream obtainable from the aqueous reaction products from the hydrogenolysis of glycerol, as represented by aqueous reaction products stream 12 in the description above) and from a lower alcohol/water stream comprised of methanol and water.

Distillate stream A was thus comprised of a nonbiobased, commercial propylene glycol doped with 100 parts per million by weight each of propylene oxide and glycidol, while distillate stream B was made up by doping not more than about 10 ppm of propylene oxide and 250 ppm of glycidol into a 2,3-butanediol cut from a distillation according to United States Patent Application Publication US 2008/0275277A1 to Kalagias. Distillate stream C was made by doping 125 ppm of propylene oxide and not more than about 10 ppm of glycidol into a methanol/water stream.

An ion exchange column was assembled by loading 100 mL of DIAION® UBK555 strongly acidic, food grade ion exchange resin from Mitsubishi Chemical Company or of AMBERLITE® 200H strongly acidic, food grade ion exchange resin from The Dow Chemical Company into an Ace Glass #15 600 mm jacketed column. The column was connected to a MasterFlex 100RPM pump and to reservoirs of Distillates A-C, the column jacket was then connected to a water bath. The resin column was washed in each iteration with 10 bed volumes of deionized water at 5 bed volumes per hour (8.3 mL/min), then 10 bed volumes of 5% hydrochloric acid solution were passed through the column, and finally an additional 10 bed volumes of deionized water were pumped through the column to rinse residual acid from the resin in question.

Feeds of Distillates A-C were then pumped through the column at the same 5 bed volumes per hour (corresponding to a column residence time of 12 minutes) rate, and the treated distillates A-C were sampled at various intervals, derivatized with diethyldithiocarbamate and analyzed for their epoxide content post-treatment, using the procedure described in Van Damme et al., "Determination of Residual Free Epoxide in Polyether Polyols by Derivatization With Diethylammonium N,N-diethyldithiocarbamate and Liquid Chromatography", Journal of Chromatography A, col. 696, no. 1, pp 41-47 (1995). The initial sampling and analysis took place after the distillates in question had passed through a single bed volume of each resin, and then typically after every 5 to 80 bed volumes (or equivalently, after intervals of from 1 to 16 hours on-stream).

It was determined by the initial sampling and analysis that there were in fact no detectable epoxides left in any of the treated Distillates A-C after only a single pass, with the limits of detection being 100 parts per billion for both epoxides in the PG product (Distillate A) by gas chromatography/mass spectroscopy, and 200-300 ppb for glycidol and 100 ppb for propylene oxide in Distillates B and C by high performance liquid chromatography (GC/MS not being well-suited for Distillates B and C because of confounding co-eluting peaks). This result demonstrates that strong acid ion exchange resins are consequently very effective in removing residual epoxides in the form of propylene oxide and glycidol from a bioderived propylene glycol.

Further sampling and analysis demonstrated that at 5 bed volumes/hr and under the other stated conditions, the DIAION® UBK555 resin was most effective for Distillate A at a temperature of 80 degrees Celsius, for Distillate B at 60 degrees Celsius and for C at from 50 to 60 degrees Celsius. No breakthrough was seen in this regard for Distillates B and C after 500 bed volumes, while Distillate A showed no breakthrough after 1600 bed volumes at 80 degrees Celsius. For the AMBERLITE® 200H resin, the preferred operating temperature was established at from 60 to 70 degrees Celsius, and no breakthrough was observed after over 2000 bed volumes had been processed of Distillate A, at 5 bed volumes per hour and at 60 to 70 degrees Celsius.

EXAMPLE 2

A simulated moving bed apparatus was configured in a 1-1-5-5 sequence to remove organic salts from an unrefined/yet-to-be-distilled PG product stream from the hydrogenolysis of glycerol over a NiRe catalyst. The apparatus employed 250 mL of DIAION® UBK550 sodium form, food grade ion exchange resin from Mitsubishi Chemical Company (the UBK550 grade corresponding to the UBK555 resin in its sodium form) in each of the twelve columns, on a carousel conventionally rotating opposite the flow of fluid through the apparatus. Five columns were used between the feed inlet to the carousel and the raffinate outlet, as an adsorption zone wherein the nonionic species (ethylene glycol, propylene glycol and glycerol) were more strongly retained and the organic salts enriched and desorbed for being continuously removed in the raffinate stream. Five columns were used between the purified, desalted product outlet and the unrefined PG feed inlet, in an enrichment zone wherein the organic salts were desorbed and the more strongly retained glycol and glycerol components enriched. One column was used between the inlet of the eluent deionized water and the purified, desalted product outlet as a desorption zone, and finally, one column was interposed as a reload zone between the adsorption zone and the desorption zone, with just enough flow through the column to displace the void fraction deionized water from the column.

The step or switch time was set at 12 minutes, with unrefined PG product containing about 25 percent of PG entering the apparatus continuously in the adsorption zone at 5.1 mL/minute. In a first run, deionized water was supplied as the eluent at 15.8 mL/minute, and the flow from the desorption zone to the enrichment zone was set at 9.7 mL/minute while the flow from the adsorption zone to the reload zone was set at 4.4 mL/minute. The raffinate and a desalted PG product flow rates from the apparatus were 10.4 and 10.5 mL/minute, respectively.

In this first run, 93.2 percent of the sodium salts were removed from the unrefined PG product into the raffinate, with an overall propylene glycol yield of 99.2 percent in the desalted PG product compared to the PG fed into the apparatus. In a second run conducted after adjusting the eluent to 15.7 mL/minute and the flow rate from the desorption zone to the enrichment section from 9.7 to 9.8 mL/minute, 96.2 percent of the sodium salts were removed into the raffinate, and 97.6 percent of the PG was retained in the desalted PG product stream.

EXAMPLE 3

An unrefined propylene glycol product was made by the hydrogenolysis of a biobased glycerol over a Ni/Re catalyst. Approximately 5200 kg of reactor product were neutralized over 19 batches. The average sulfuric acid dosage was 0.33 g/100 g of feed. There were two batches where the sulfuric acid loading was significantly less (0.03 g/100 g). The cause was undetermined, but may have been due to low concentration of propylene glycol due to start-up or shut down of the reactor. The average pH of the reactor product was 12.1 and the average neutralized pH was 6.9.

The thus-neutralized product was then distilled according to the embodiment shown in FIG. 2, beginning with an alcohol removal step. This column was run under atmospheric pressure. Due to equipment constraints a high reflux ratio was used. This resulted in less water overhead (4-12 wt %) than indicated by process modeling (27 wt %). The propylene glycol yield was >99%. The other parameters are given in the table below.

TABLE 1

Alcohol Removal summary

|  | Alcohol Pilot | ASPEN |  |
|---|---|---|---|
| Rebolier temp | 215 | 218 | F. |
| Overhead temp | 155-160 | 180 | F. |
| Overhead pressure | atmospheric | atmospheric |  |
| Reboiler pressure | atmospheric | atmospheric |  |
| PG yield | >99% | 100% |  |
| Reflux ratio | 70-400 | 10 |  |
| Overhead H2O | 4-12% | 27% |  |
| Bottoms Alcohol | 100-200* | 1000 | ppm |

*as low as 10, one excursion as high as 800

The next step was a primary water removal step, designed to remove substantially all of the water so that the bottoms to a subsequent glycerol removal step would contain less than 1 wt % of water. This step was completed successfully. The water concentration was brought down to 0.6%. The propylene glycol yield was >99%. There were several operational problems due to salts in the reboiler and feed lines, but these were mainly believed to be due to not having the correct steam flow or other operational issues. There was no evidence of solids formation in the packing, which had been a concern with the low levels of water targeted. The salts would wash out easily with water, and the column was continuously run for approximately 5 days without having problems with the solids. The results are given in the table below.

TABLE 2

Water Removal Column (WRC) Performance

|  | WRC Pilot | ASPEN |  |
|---|---|---|---|
| Reboiler temp | 340-355 | 342 | F. |
| Overhead temp | 196-200 | 193 | F. |
| Overhead pressure | 20.4 | 20.4 | In of Hg |

TABLE 2-continued

Water Removal Column (WRC) Performance

|  | WRC Pilot | ASPEN |  |
|---|---|---|---|
| Reboiler pressure | 20.5-23 | 22.8 | In of Hg |
| PG yield | >99% | 100% |  |
| Reflux ratio | NA | 0.4 | reflux too low for pilot meter |
| Bottoms H2O | 0.6-1.1 | 1% |  |

The next separation was to remove the residual unreacted glycerol in a glycerol removal step. This step went very smoothly with no significant problems. The yield was >99% with 0.5% glycerol in the distillate. Other conditions and results were as reported in Table 3:

TABLE 3

Glycerol Removal Column (GRC) Performance

|  | GRC Pilot | ASPEN |  |
|---|---|---|---|
| Reboiler temp | 322-338 | 323 | F. |
| Overhead temp | 204-210 | 208 | F. |
| Overhead pressure | ~1-2 | 0.8 | In of Hg |
| Reboiler pressure | NA | 1 | In of Hg |
| PG yield | >99% | 100% |  |
| Reflux ratio | 1-4 | 0.4 |  |
| Dist. Glycerol | <0.5% | 2% |  |

Ethylene glycol was next to be separated out as a principal component of the PG product mixture. The results were not as good as hoped, unfortunately, primarily due to operational error. The goal was to maximize yield and the distillate that went forward was not within specification (600 ppm on a propylene glycol basis). There was also one upset that caused ethylene glycol at 1.2% to go forward. Propylene glycol yield was between 95 and 98%, and the bulk product forward for the subsequent butanediol removal step had 5700 ppm ethylene glycol and 200 ppm 1,2-butanediol, as compared to the 500 ppm ethylene glycol and 50 ppm 1,2-butanediol expected from modeling. During the run, the ethylene glycol concentration was brought to approximately 45%, indicating that the amount of ethylene glycol in the feed has an effect on the propylene glycol yield. This column was run at 15.6 in Hg absolute pressure. The results are given in the table below.

TABLE 4

Ethylene Glycol Removal Column (EGRC) Performance

|  | EGRC Pilot | ASPEN |  |
|---|---|---|---|
| Reboiler temp | 341-346 | 326 | F. |
| Overhead temp | 324-326 | 311 | F. |
| Overhead pressure | 15.3 | 10.2 | In of Hg |
| Reboiler pressure | 16.6 | 11.2 | In of Hg |
| PG yield | 95-98 | 90% |  |
| Reflux ratio | 3-8 | 8.5 |  |
| Dist EG | 1200-1700* | 156 |  |
| Bottoms EG | 40-46% | 22% |  |

*One run was as low as 540 ppm

The final distillation step undertaken was for the removal of 2,3-butanediol (and 2,3-pentanediol and other lighter impurities). The goal of this step was to take USP grade propylene glycol as a bottoms product with less than 1000 ppm total butanediols and pentanediols. This specification was met, even with the additional 1,2-butanediol from errors in the previous step. The yield was 95-97%. The column was run at 10.7 in Hg absolute pressure. The final product had no detectable epoxides (0.2 ppm LOD). The results are summarized in the table below. The APHA color of the samples of the bottoms product was 3 and the specification was 10. A sample of the final propylene glycol product was given to a sensory group and found to be satisfactory.

TABLE 5

Butanediol Removal Column (BRC) Performance

|  | BRC Pilot | ASPEN | |
| --- | --- | --- | --- |
| Reboiler temp | 325 | 299 | F. |
| Overhead temp | 197-218 | 264 | F. |
| Overhead pressure | 10.7 | 6.1 | In of Hg |
| Reboiler pressure | 13.7-14 | 7.7 | In of Hg |
| PG yield | 95-97% | 97% | |
| Reflux ratio | 80-90* | 35 | |
| Bott total diols | 950-1000** | <1 ppm | |

*Reflux ratio will vary greatly due to the relatively low distillate rate
**200 ppm was 1,2-BDO which is normally removed with EG, however an upset sent some forward.

What is claimed is:

1. A process for producing a biobased propylene glycol product by reacting an aqueous solution of glycerol with hydrogen to produce a crude product mixture including water, lower molecular weight alcohols, higher diols, unconverted glycerol and one or both of propylene oxide and glycidol, then removing water, lower molecular weight alcohols, higher diols and unconverted glycerol from the crude product mixture to produce a finished propylene glycol product having an APHA of 10 or less, characterized in that a further purification is undertaken to reduce the concentration of at least one of propylene oxide and glycidol in the finished propylene glycol product having an APHA of 10 or less and a purity of at least 95% by contacting the same with a strong acid ion exchange resin.

2. A process according to claim 1, wherein one or both of the propylene oxide and glycidol are present in the finished propylene glycol product prior to the further purification at more than 100 parts per million, and after the further purification one or both are present at less than 100 parts per billion.

* * * * *